United States Patent [19]

Atwood et al.

[11] 4,076,503
[45] Feb. 28, 1978

[54] PIPETTING SYSTEM FOR USE IN KINETIC ANALYSIS APPARATUS AND THE LIKE

[75] Inventors: John G. Atwood; Charles F. DeMey, III, both of Redding; Hamilton W. Marshall, Jr., Ridgefield; Lucien C. Ducret, Riverside, all of Conn.

[73] Assignee: The Perkin-Elmer Corporation, Norwalk, Conn.

[21] Appl. No.: 640,459

[22] Filed: Dec. 15, 1975

Related U.S. Application Data

[63] Continuation of Ser. No. 499,792, Aug. 22, 1974, abandoned.

[51] Int. Cl.² .............................................. G01N 1/10
[52] U.S. Cl. ................................... 23/259; 23/253 R; 73/425.4 P; 141/90
[58] Field of Search ................ 23/253 R, 259, 230 A; 73/425.4 P, 425.6; 222/148; 141/86, 88, 90

[56] References Cited

U.S. PATENT DOCUMENTS

| | | | |
|---|---|---|---|
| 2,879,141 | 3/1959 | Skeggs | 23/253 R |
| 3,143,393 | 8/1964 | Hons | 23/253 R |
| 3,252,330 | 5/1966 | Kling | 23/253 R X |
| 3,484,207 | 12/1969 | Anthon | 23/259 X |
| 3,552,212 | 1/1971 | Ohlin | 23/259 UX |
| 3,572,998 | 3/1971 | Anthon | 23/259 |
| 3,601,162 | 8/1971 | Page | 141/90 |
| 3,756,783 | 9/1973 | Williams | 23/259 X |
| 3,768,526 | 10/1973 | Sanz et al. | 23/253 R X |
| 3,800,984 | 4/1974 | Phelan | 23/259 |
| 3,900,289 | 8/1975 | Liston | 23/259 X |
| 3,981,041 | 9/1976 | Atwood et al. | 15/302 |

*Primary Examiner*—Morris O. Wolk
*Assistant Examiner*—Arnold Turk
*Attorney, Agent, or Firm*—S. A. Giarratana; F. L. Masselle

[57] ABSTRACT

An automatic pipetting system for pipetting a measured micro-quantity of reagent into a reaction cup, in which the pipetter is lowered into a reagent bottle, a predetermined amount of reagent drawn in using a positive displacement pump, the pipetter withdrawn from the reagent bottle through an irrigated wiping sponge to accurately control the drop of reagent at its tip, rotated to a position over the cup and lowered thereinto after which the displacement pump expels a measured amount of reagent.

4 Claims, 6 Drawing Figures

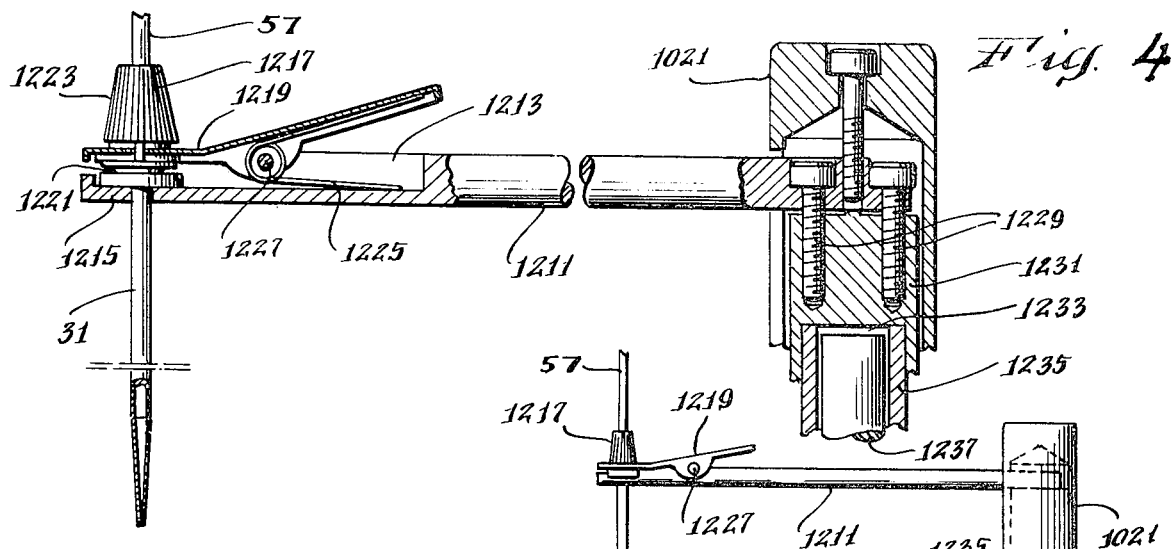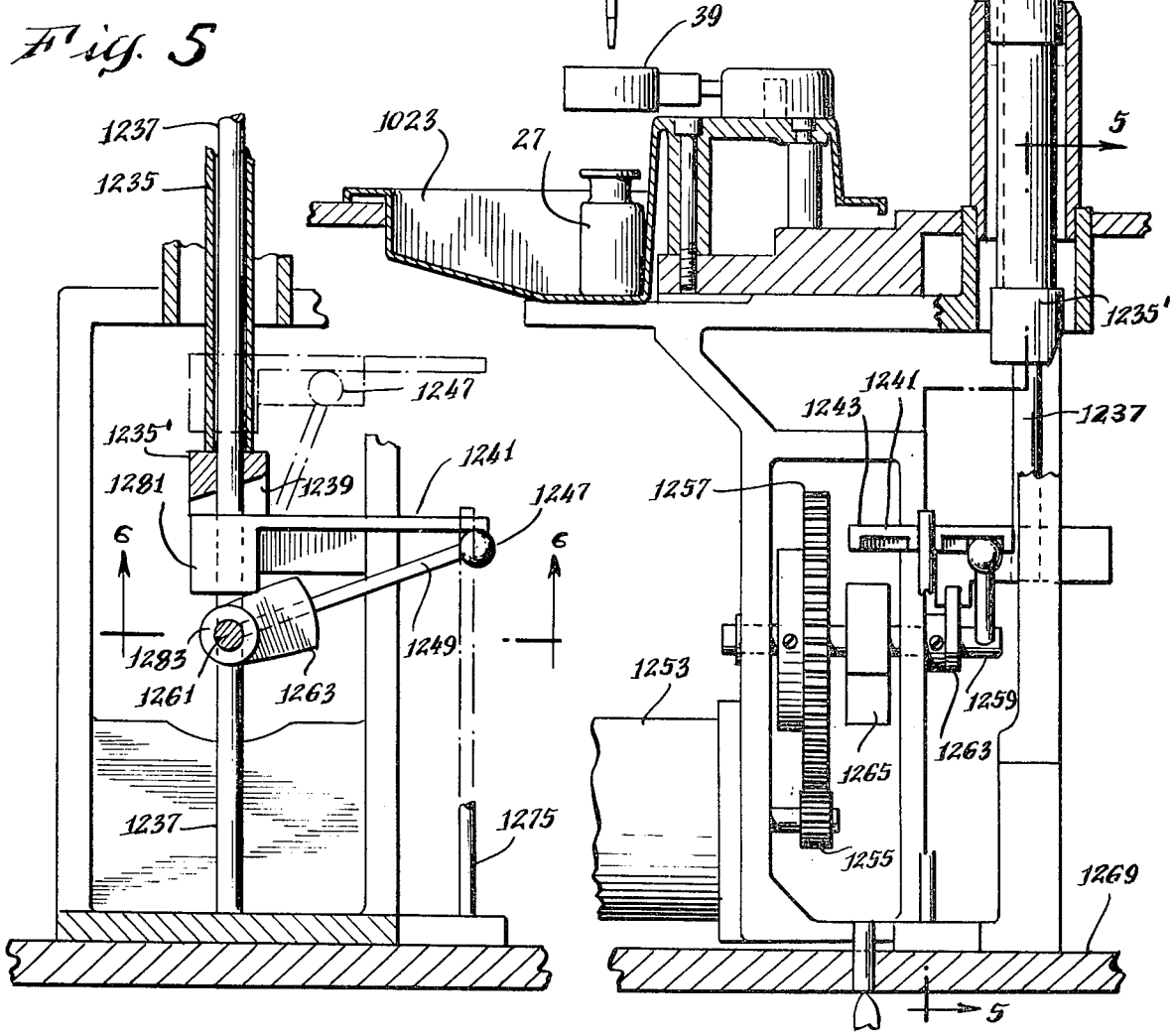

4,076,503

PIPETTING SYSTEM FOR USE IN KINETIC ANALYSIS APPARATUS AND THE LIKE

BACKGROUND OF THE INVENTION

This application is a continuation of Ser. No. 499,792 filed on Aug. 22, 1974, and now abandoned.

This invention relates to analysis apparatus in general and more particularly to an improved automatic system for pipetting controlled quantities of a reagent or the like.

In an application Ser. No. 594,951, filed July 10, 1975 as a continuation of now-abandoned application of John G. Atwood et al, Ser. No. 499,602 filed Aug. 22, 1974 and assigned to the same assignee as the present invention, a completely automated kinetic analysis apparatus is disclosed. One of the basic elements permitting that apparatus to operate in an accurate and reliable manner is an automatic reagent pipetting system. The disclosed analysis apparatus operates using micro-quantities of reagent and serum. As a result, it is necessary that the amount of reagent pipetted into a reaction vessel in which it is mixed with the serum to start a reaction to be accurately controlled to the highest possible degree. Furthermore, the pipetting operation must take place automatically and efficiently.

In apparatus of the type disclosed, different tests must be run requiring a quick changeover of reagents. The approach taken in prior art apparatus to the problem of analysis of this nature was to use relatively large quantities of reagents and the like so that any lack of accuracy or repeatability would not seriously affect the results. Furthermore, changeover of reagents in prior art apparatus was not easily accomplished and, in some cases, a plurality of pipetting means were used to overcome these problems.

In view of these deficiencies, it is the object of the present invention to provide a pipetting system which operates automatically and pipettes accurately controlled amounts of reagent in a repeatable manner, doing this automatically and at the same time providing a capability for quick changeover of reagents.

SUMMARY OF THE INVENTION

The pipetting system of the present invention includes a number of features which enables it to provide the required accuracy, repeatability, reliability and flexibility.

No reagent is stored in any of the tubes in the system, reagent being in contact only with an easily exchangeable pipette. This permits an easy changeover of reagents by simply changing reagent bottles and pipettes thereby simplifying the running of different tests. An irrigated sponge is used to wipe the tip of the pipette to insure that a precise volume is delivered, to reduce carryover and to dispose of small amounts of reagent wasted each cycle. Reagent is pipetted directly out of the bottles in which it is reconstituted from the freeze-dried state in which it is packaged.

The pipetting system comprises a mechanism that moves an exchangeable pipette between a reagent supply container and the reaction vessel in a cyclic manner. The pipette is connected by a long thin flexible tube filled with air to a cam-driven valveless displacement piston and cylinder pump assembly, the operation of which is coordinated with the pipette-moving mechanism. The cycle starts in a rest position with the pipette penetrating the irrigated sponge wiper with its tip just below the sponge but not in the reagent container, the cycle including the following steps:

(a) the pipette descends into the reagent supply;
(b) the pump assembly causes the pipette to take up the required reagent volume plus a small extra volume for margin;
(c) the pipette withdraws from the wiper sponge, wiping off the outside of the pipette tip;
(d) the pipette moves to, and descends into, the reaction mixture cup decending to a level such that after expelling reagent, the tip will be in contact with the resulting liquid surface in the reaction vessel;
(e) the pump assembly causes expulsion of the required volume into the reaction vessel;
(f) the pipette ascends, returns to the sponge wiper and stops directly over it, without penetrating;
(g) the pump assembly causes expulsion of a reagent volume slightly greater than the extra volume for margin, thus cleaning any carry-back of the reaction vessel contents that may have entered the pipette tip;
(h) the pipette descends through the wiper sponge to rest position above the reagent, thus wiping off any carry-back from the outside of the pipette;
(i) the pump assembly causes inspiration of a volume of air required to return it to its starting position, thus ending the cycle.

This cycle has the effect of very precise volume delivery because of wiping of the pipette tip, and because the volume delivery does not require total clearing of the tip, since part of the extra volume for margin may "hang up" inside the pipette without affecting the volume delivered.

The cycle gives very low carryover because the expulsion of the extra volume as waste into the sponge wiper cleans the inside of the pipette and the sponge itself cleans the ouside.

BRIEF DESCRIPTION OF THE DRAWINGS

FIG. 3 is an elevational view partially in section, illustrating the pipetting mechanism of the present invention;

FIG. 4 is a detailed sectional view on an enlarged scale of the uppermost portion of FIG. 3;

FIG. 5 is a sectional view on line 5—5 of FIG. 3; and

DETAILED DESCRIPTION OF THE PREFERRED EMBODIMENT

As noted above, the pipetting system of the present invention is particularly useful in kinetic analysis apparatus such as that disclosed in the aforementioned copending application Ser. No. 594,951. The disclosure of that application will be helpful to an understanding of the pipetting system of the present invention and its interrelation with a completely automatic analysis apparatus. As particularized in a further application of John G. Atwood et al, Ser. No. 499,596 filed August 22, 1974, now Pat. No. 3,948,605, and assigned to the same assignee as the present invention, the complete apparatus embodies an additional pipetting system combined with a diluent supply pump for automatically taking up and diluting serum samples. The present invention relates to the reagent pipetting system albeit disclosed in conjunction with the sample dilution and pipetting system of the aforementioned analytical apparatus. Unless otherwise specified or appearing from the context, references herein to a pipetting system shall mean the (reagent) pipetting system of the present invention.

Figure 1:
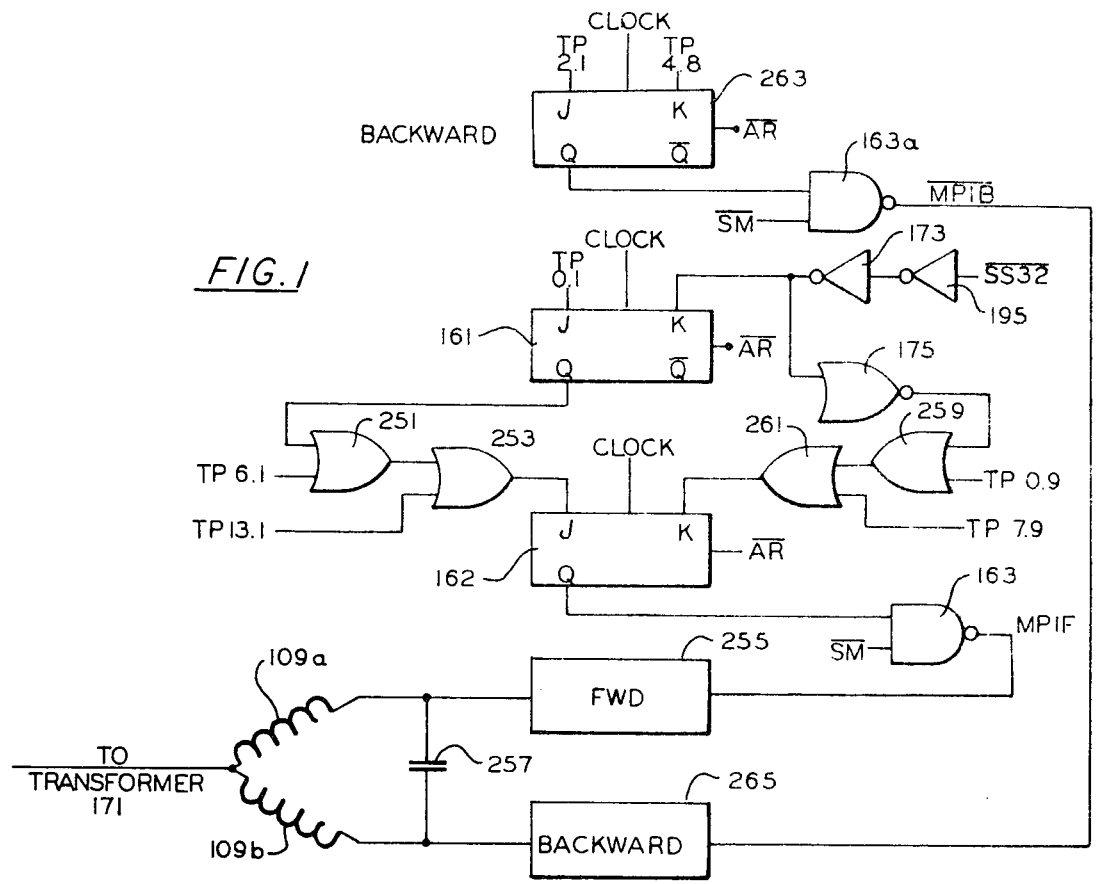
FIG. 1 is a logic diagram for the control logic of the pipetting system.

As will be described in greater detail hereinafter in this specification, the motive power for operating the pipetting system is supplied by a bi-directional electric motor 1253 shown in FIG. 3 and associated with the logic circuitry of FIG. 1. Also associated with and controlled by suitable circuitry is a motor 501 (FIG. 2) which operates pumps for the sample dilution and the pipetting system as hereinafter to be explained.

Before describing the pipette operating mechanism, this logic circuitry for controlling the pipetting movement and the operating cycle of the system will be described with reference to Table 1, hereinbelow, and FIG. 1 of the drawings.

In the pipetting cycle, as shwon on Table 1, it is desired to start a forward motion of motor 1253 at the time of 0.1 second. Thus, a 0.1 second output from a timer and control unit (not shown), fully described in the aforementioned copending application Ser. No. 594,951, is provided as the set or J input to flipflop 161. When a clock pulse appears, a flipflop 161 is set. This results in Q output of "1" which is one input to an OR gate 251. The second input to OR gate 251 is from the 6.1 second output of the control unit.

Previously, both inputs were "0" and the output of gate 251 was a "0". Its output now goes to "1". This output is one input to an OR gate 253 which has as its other input the 13.1 second output of the control unit. This output will be "0". Thus, the output of gate 253 will go to a "1", flipflop 162 will be set and, through a gate 163, will provide an input to a triac motor control 255. The motor in this case has two windings designated 109a and 109b with a capacitor 257 across or in parallel with the windings. Winding 109a is arranged to cause forward rotation of the motor and winding 109b reverse rotation. The output of gate 163 will fire triac motor control 255 causing the motor to rotate in a forward direction. This will cause the pipette (pipette 31, shown in FIGS. 2 and 3) to be lowered into the reaction supply in a manner to be described presently. In the meantime, flipflop 161 has been reset through a Schmitt trigger 195 and inverter 173 so that the Q output flipflop is a "0".

At time 0.9 seconds, sufficient lowering of the pipette will have taken place and the motor (1253) is to be stopped. This is accomplished through the 0.9 input from the control unit to an OR gate 259. This input will cause its output to become "1" causing the output of an OR gate 261 to have one "1" input and to provide a "1" input to the K or reset input of flipflop 162. Motor 1253 will stop and another motor (501) associated with the pumping assembly (FIG. 2) will cause reagent to be drawn into the pipette using a vacuum pump to be described presently. This will have been accomplished by the time 2.1 seconds, at which point, it is desired to withdraw the pipette. This withdrawal movement causes the pipette to be raised and then rotated to a position over, and lowered into, a reaction vessel. To this end, a further flipflop 263 is provided having as its set input the 2.1 second output of the control unit. The Q output of flipflop 263 is provided to a gate 163a operating in the same manner as gate 163 to initiate the firing of a second triac circuit 265 to cause a flow of current through the reverse winding 109b of motor 1253. The motor turns in a reverse direction until time 4.8 seconds when a corresponding output from the control unit is used to reset flipflop 263 causing the output of gate 163a to change and turn off the triac circuit, stopping the motor.

At time 6.1, an input from the control unit is provided into the gate 251 causing its output to go from "0" to "1". Again, with one "1" input, gate 253 will have a "1" output causing flipflop 162 to be set to begin forward motion in the manner described above. This forward motion continues until time 7.9 seconds when an input to gate 261 results in an output therefrom resetting the flipflop. The pipette is now positioned at a wiper sponge unit (39, FIG. 3) where any remaining reagent is discharged. After discharge at time 13.1 seconds, forward motion is started again by the 13.1 output of the control unit, provided as an input to gate 253. Rotation continues until a position sensor SS32 is encountered and generates a signal at which point, the changing output of Schmitt trigger 195 and inverter 173 through gates 175, 259, and 261 resets flipflop 162. Thus throughout the cycle, starting and stopping is controlled by the control unit; however, the end of the cycle and the position at which the motor is stopped is controlled by an angular position sensor sensing the exact motor position as more fully described in the above-referenced application Ser. No. 594,951. This insures accurate repeatability from cycle to cycle. The cycle carried out in the sample dilution and reagent pipetting system is given by the table below. Operation of the diluent and reagent pump drives and diluter probe drive is essentially the same as that described for the pipetting system.

TABLE 1

| Time (Real) | Action |
| --- | --- |
| 0.1 | Start Pipette |
| 0.9 | 1) Stop Pipette |
|  | 2) Start Diluter Pump |
| 1.5 | Start Diluter Probe |
| 2.1 | Start Pipette |
| 3.4 | Stop Diluter Pump |
| 4.0 | Stop Diluter Probe |
| 4.6 | Start Diluter Pump |
| 4.8 | Stop Pipette |
| 6.1 | 1) Start Diluter Probe |
|  | 2) Start Pipette |
|  | 3) Stop Diluter Pump |
| 7.9 | Stop Pipette |
| 10.1 | 1) Start Diluter Pump |
|  | 2) Check mode |
| 10.9 | 1) Stop Diluter Pump |
|  | 2) Start Table |
| 13.1 | Start Pipette |
| 13.5 | Start Diluter Probe |
| 13.9 | Stop Diluter Pump |
| 15.4 | 1) Start Diluter Pump |
|  | 2) Move, Go |
| 16.8 | End of Cycle |

Figure 2:
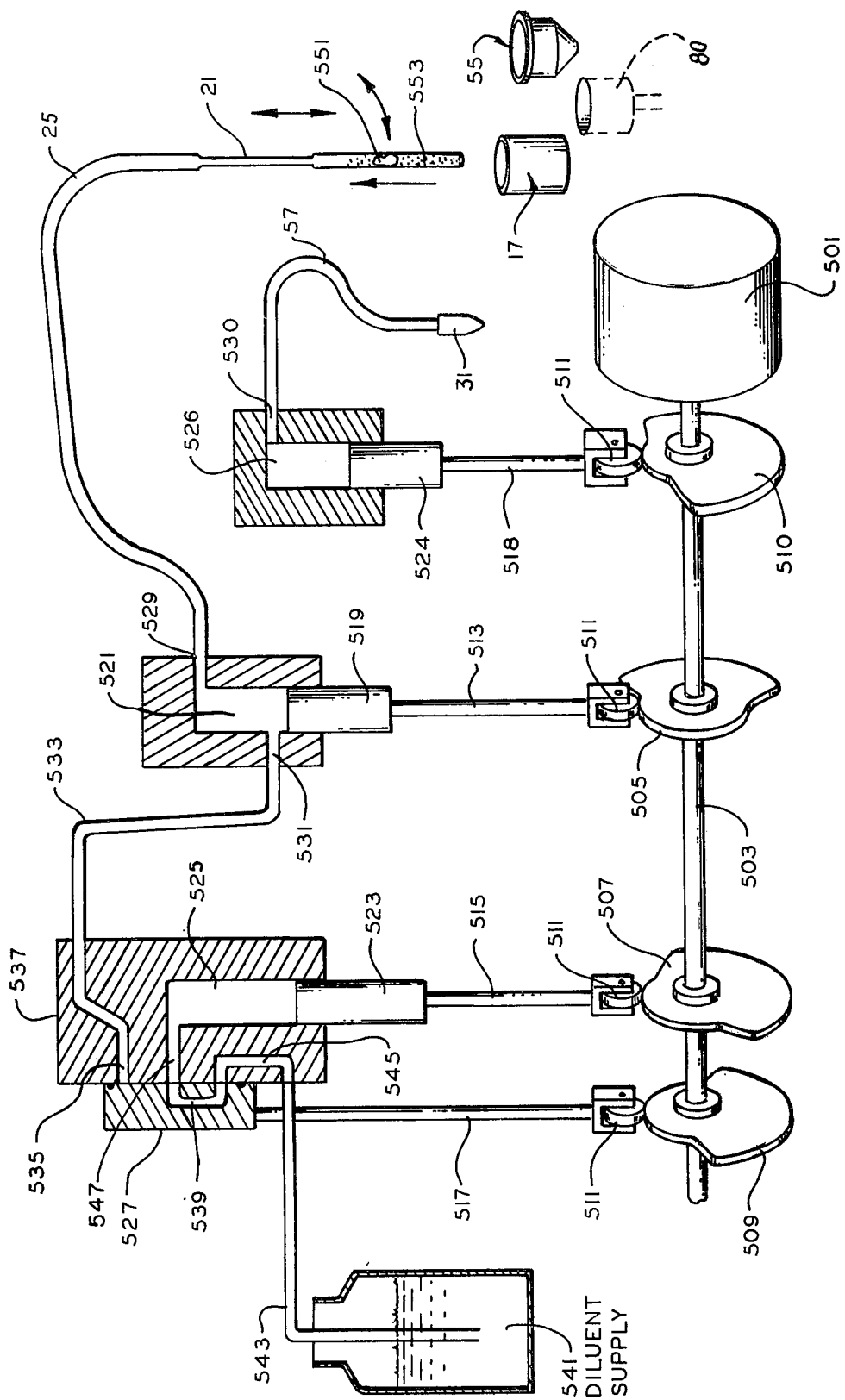
FIG. 2 is a schematic illustration of a diluting pump and the pipetting pump systems of the present invention.

FIG. 2 is a schematic perspective view illustrating the pipetting system, as well as the sample dilution system with which it is interrelated. These systems include a motor 501 energized and driven by a circuit such as that first described with reference to FIG. 1. Reference should also be had to Table 1, above, which indicates the cycles of operation. On the shaft 503 of motor 501 are four cams 505, 507, 509 and 510; engaging the profile of each of the cams are respective cam followers 511 attached to push rods 513, 515 and 518. On the ends of rods 513, 515, and 518 are respective pistons 519, 523, and 524 operating within cylinder bores 521, 525, and 526. Rod 517 has on its end a slide valve member 527. Cylinder bore 521 has a port 529 which is coupled by a flexible tube 25 to a sample probe 21. Another port 531 in cylinder 521 is coupled by a flexible conduit 533 to a passage 535 in the block 537 containing cyclinder bore 525. When slide valve member 527 is in its uppermost position, passage 535 is coupled through a valve member passage 539 to a port 547 opening into cylinder bore 525. A container 541 filled with diluent is coupled through an appropriate conduit 543 to a further passage 545 in block 537 which is coupled to cylinder port 547 via passage 539 when slide valve member 527 is in its lowermost position as depicted in FIG. 2.

A port 530 connects cylinder bore 526 via a flexible tube 57 to pipette 31. Piston 523 and cylinder bore 525 constitute the diluter pump and piston 519 and cylinder bore 521 the pump for drawing samples of serum. Piston 524 and cylinder bore 526 form the pump for the reagent pipetting system.

As shown in Table 1, at time 0.1 the pipette drive is started to move pipette 31 into position in a reagent container (27, FIG. 3); at time 0.9, the pipette motion is stopped and the diluter pump started. Motor 501 rotates cam 510 causing pipette pump piston 524 to move downward drawing reagent into pipette 31. The pipetting system contains only air with a partial vacuum being created by the piston motion to draw the reagent into the pipette 31. Thus, reagent is present only within interchangeable glass pipette 31. At time 1.5, sample probe 21 is actuated with its drive mechanism moving it from the resting position over a flushing station 80 to a position over a sample container 17. At time 2.1, pipette 31 is started again to withdraw it from reagent container 27 to a position over reaction vessel 55. At time 3.4, the diluter pump is stopped and at time 4.0, sample probe 21 is stopped.

At the beginning of the cycle, piston 519 was at the upper limit of travel. At time 2.1, when the pipette drive starts to withdraw pipette 31 from the reagent bottle 27 and move it to reaction vessel 55, a flat on its associated cam 510 is reached to stop downward travel of piston 524 and thus prevent further intake of reagent. Rotation of the shaft 503 continues, however, to drive the cam 505 associated with the sample pump piston 519 to cause a small air bubble 551 to be drawn into sample probe 21 before it reaches the serum sample. At time 4.0, sample probe 21 is stopped in the serum sample and at time 4.6, the diluter pump restarted. At time 4.8, the motion of pipette 31 is stopped, now in position over the reaction vessel. Restarting of the diluter pump results in piston 519 being moved farther down in bore 521 to draw into sample probe 21 the required amount of serum 553.

During operation of the diluter system including the sample pump and diluent pump, all conduits are continuously filled with diluent except for the air bubble 551 described above. Thus, as the piston 519 is drawn farther down into the cylinder 521, diluent in tube 25 will be drawn from tube 25 into the cylinder and the remainder of the tube will be filled with diluent except for the air bubble 551 and the serum sample 553. Following time 4.8 when the pipetter displacement system is stopped, rotation of the cam 510 will drive pipette pump piston 524 upward to discharge the reagent contained within pipette 31. At time 6.1, sample probe motion resumes, pipetter 31 starts back to the reagent supply bottle 27 and the diluter pump is stopped. At this time, a full sample will be in probe 21.

During this initial portion of the cycle, valve member 527 was maintained in its lowermost position as shown in FIG. 2 and piston 523 moved from its uppermost to its lowermost position drawing diluent from container 541 through conduit 543, passage 545, valve member 527 and port 547 into cylinder bore 525. Sample probe 21 which started movement at time 6.1 is raised and rotated to a position over reaction vessel 55. At time 7.9, pipette 31 stops over the reagent supply. At time 10.1, motor 501 is restarted causing valve member 527 to move to the upper position so that valve passage 539 couples passage 535 and port 547. Also at this time, a small amount of remaining reagent is discharged from pipette 31 to an associated sponge (unit 39, FIG. 3). At this point, sample probe 21 is moving down into reaction vessel 55; the probe is stopped at 10.9 but the diluter pump continues to run, cam 507 driving piston 523 upward. Piston 519 is now in the position shown in FIG. 2 so that the diluent is pumped out of the cylinder 525 through the port 547, valve passage 539, passage 535, and conduit 555 into cylinder 521 and thence through the port 529 into flexible tube 25. This results in the serum sample being pumped into reaction vessel 55. Because of the greater displacement of the piston 523 as compared to 521, not only is the sample pumped out but a measured quantity of diluent along with it. However, diluter pump piston 523 is not moved all the way up during this cycle but is stopped in a mid-stroke position. It will be understood that, at this time, the complete (except for pipette cylinder 526 and conduit 57) system contains diluent. At time 13.5, the sample probe is started again and at time 13.9, the diluter pump stopped. The probe rotates until it is over flushing station 80 and stops whereupon, at time 15.4, the diluter pump is restarted, piston 523 moving to the top of its stroke to rinse out the probe. Motor 501 then stops, halting the diluter pump with its piston (523) at the top of its stroke. This occurs approximately at time 16.8 which is the end of the cycle. Motor 501 is then ready to start another cycle in response to a new control unit output.

FIGS. 3-6 illustrate the apparatus used for obtaining the required pipette motion. As described above, pipette 31 must have the capability of moving up and down at both ends of its rotation between reagent container 27 and the reaction vessel 55. This combined rotation and up and down movement is accomplished through the use of a butterfly cam. FIG. 3 is an elevational view, partially in section, of the pipette displacement mechanism. Reagent container 27 is disposed within a well 1023. A pipette wiper unit 39 is provided so that the pipette tip 31 is wiped as it passes through the sponge (not shown) embodied in the unit. The sponge is irrigated within the wiper unit 39 which may be structured either conventionally within the prior art or as described in the aforementioned application Ser. No. 594,951 and claimed in U.S. Pat. No. 3,981,041. Pipette 31 is supported on a cantilever arm 1211 shown in greater detail in FIG. 4. At its free end, arm 1211 contains a flat recess 1213 and at the very end has a slotted portion 1215 to permit insertion of the removable pipette 31. Pipette 31 is held in place by a spring loaded rubber grommet 1217. The grommet 1217 has a portion passing through a suitably apertured lever 1219. The bottom part 1221 of the grommet rests against the top of pipette 31 sealing it in place. Flexible tube 57 is inserted into the top part 1223 of the grommet 1217 down to the level shown in dotted lines. A spring 1225 is provided to bias the lever 1219 upward at its right-hand side. This causes the member 1219 which rotates about a pivot point 1227 to exert a downward pressure on the grommet 1217 pushing its bottom part 1221 against pipette 31 holding it in place and sealing it.

The arm 1211 is bolted, using bolts 1229, to a member 1231 essentially cylindrical in shape. Member 1231 has a cylindrical recess 1233 therein into which is press fitted a hollow cylindrical member 1235. Within cylindrical member 1235 is a rod 1237 which is fixed to the base 1269 of the apparatus. Members 1235 and 1231 are free to rotate as a unit about the rod 1237.

Member 1235 terminates at its base in a larger cylindrical portion 1235' having a slanted cut thereon mating with a cylindrical projection 1239 on a butterfly cam member 1241 as shown in FIG. 5. Cam 1241 is also free to rotate about and move up and down on the rod 1237. It can be seen that motion of butterfly cam 1241 up and down and rotationally about the rod 1237 results in corresponding motion of the arm 1211 and pipette 31. The slanted coupling between the members 1235 and 1239 permits manually raising and rotating the arm 1211 without engagement with the butterfly cam 1241 for maintenance purposes. It also eases the positioning of the arm 1211 for changing pipettes 31.

Figure 6:
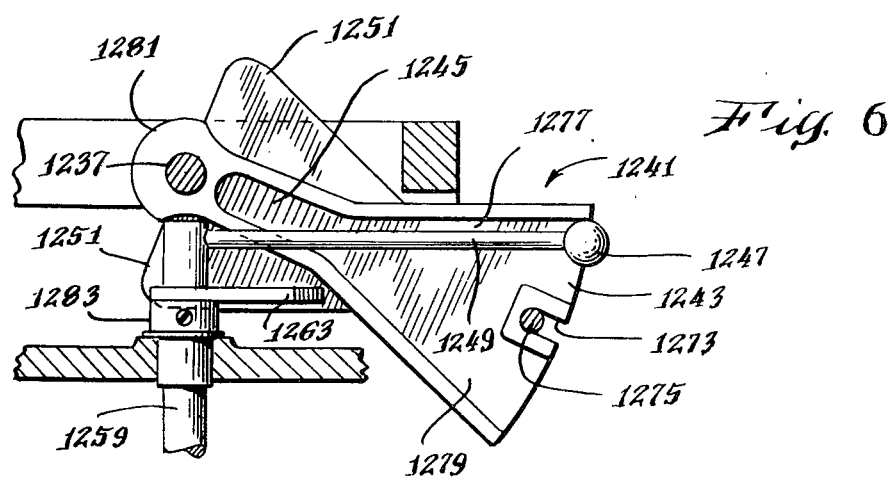
FIG. 6 is a view partly in section on line 6—6 of FIG. 5 looking in the direction of the arrows.

The details of construction of butterfly cam 1241 are shown in FIG. 6, a plan view of its underside. As can be seen from that view, and also with reference to FIG. 3, cam 1241 contains in its underside a recess 1243. This recess includes a divergent portion narrowing to a channel portion 1245. Motion of cam 1241 is obtained by movement of a ball 1247 on the end of a rod 1249. Butterfly cam 1241 also contains projections 1251 on each side the purpose of which will become evident presently. Rod 1249 is driven by motor 1253 (shown in FIG. 3) and previously alluded to in conjunction with the FIG. 1 logic circuitry, through gears 1255 and 1257. Rod 1247 is affixed to a shaft 1259 which is attached to gear 1257. Shaft 1259 is supported in conventional bearing means for rotation about an axis 1261 (FIG. 5). Also attached to the shaft 1259 is a cam 1263 which engages the projections 1251 in a manner to be described below. Also mounted on the shaft 1259 is a retro-reflector element 1265 which is used in connection with a sensor system for stopping the cycle in the manner described above. For additional details of the sensor system, reference may be had to the aforementioned co-pending application Ser. No. 594,951 as well as to an application of John G. Atwood et al, Ser. No. 499,595 filed Aug. 22, 1974 entitled Angular Sensor. The butterfly also contains notch 1273 in its end which, in a lower position, engages a pin 1275 used for smoothly guiding the butterfly as it is lowered.

The manner in which the apparatus operates may best be understood by going through a cycle of operation. In the positions shown in FIGS. 3, 5 and 6, ball 1247 is just starting to move the butterfly 1241. As rod 1249 is rotated counterclockwise, it will ride within the recess 1243 against the edge 1277 of the butterfly raising the butterfly upward and with it, arm 1211 and pipette 31. When rod 1249 gets to cam portion 1245, it will cause rotation of the butterfly 1241 about the rod 1237 resulting in rotation of the arm 1211 and pipette 31. Rotation will continue over an angle determined by the length of the channel 1245 with the ball, at a point half way through the angle, beginning motion down the side 1279 of the butterfly; as the ball gets to the angled portion of that side, the butterfly will begin to be lowered, i.e., the ball will move along edge 1279 lowering the butterfly and with it the arm 1211 and pipette 31. As butterfly 1241 gets down to the position shown in FIG. 5, (it will be in this position but on the other side, having seen rotated) it will engage the pin 1275 for guidance purposes. Eventually, ball 1247 will lose contact with the butterfly as the base portion 1281 comes to rest on cam 1263. Thereafter, cam 1263 will then control the further descent of pipette into contact with the liquid in either the reagent bottle or reaction vessel as the case may be. The profile of cam 1263, in particular the surface 1283, controls this final lowering into the desired position by riding on butterfly cam projections 1251 (on one side or the other). For rotation back to the position shown, the opposite chain of events takes place: rod 1249 and cam 1263 rotate clockwise, the cam 1263 first pushing the butterfly 1241 upward until the ball 1247 engages the butterfly with the ball then pushing it upward to the position shown in dotted lines after which it rotates the butterfly then lowers it back onto the cam 1263.

Thus, an improved pipetter for use in automatic analysis apparatus has been shown. Although specified embodiments have been illustrated and described, it will be obvious to those skilled in the art that various modifications may be made without departing from the spirit of the invention which is intended to be limited solely by the appended claims.

What is claimed is:

1. Apparatus for transferring a liquid reagent from a reagent container to a reaction vessel comprising:
   (a) a pipette having a storage volume at least equal the volume to be taken from said reagent container;
   (b) pump means including a piston and a cylinder;
   (c) a flexible conduit filled with air coupling said pipette to said pump means;
   (d) means for positioning said pipette vertically and rotationally in a horizontal plane to locate said pipette above said reagent container or in either said reagent container or said reaction vessel;
   (e) means for absorbing liquid disposed over said reagent container in the path of travel of the pipette to and from said reagent container said aborbing means being an irrigated sponge which is penetrable by said pipette in both directions travelled thereby to wipe the outer portions thereof; and
   (f) means for controlling said pump means to cause said pipette to draw in reagent in excess of the required reagent volume to be deposited in the reaction vessel, to cause said pipette to discharge only the required amount of reagent into said reaction vessel, and then to cause said pipette to expel the excess volume onto said absorbing means when located above said reagent container.

2. Apparatus as in claim 1 wherein said pipette positioning means comprise:
   (a) a central shaft mounted for vertical axial translation and rotational movement;
   (b) a cantilever arm attached to one end of said shaft, the pipette being attached to the free end of the arm; and
   (c) means to rotate and axially displace said shaft.

3. Apparatus as in claim 2 wherein said means to rotate and axially displace said central shaft comprise:
   (a) a butterfly cam member having channels on its underside coupled to said central shaft;
   (b) a motor drive means having a drive shaft; and
   (c) an arm having one end coupled to said drive shaft and terminating at its other end in a ball resting in said channels, rotation of said arm causing said butterfly cam and the central shaft therewith to first be pushed upward and then rotated and then lowered in response to rotation of said drive shaft.

4. Apparatus as in claim 3 wherein said butterfly cam contains a further cam follower surface and said apparatus further includes a cam on said drive shaft arranged to contact the follower surface on said butterfly cam at a point of rotation where the ball on said arm looses contact with said butterfly cam, further rotation of said drive shaft causing a further lowering of said butterfly cam and said central shaft whereby the final lowering of said pipette is accurately controlled.

* * * * *

UNITED STATES PATENT AND TRADEMARK OFFICE
CERTIFICATE OF CORRECTION

PATENT NO. : 4,076,503

DATED : February 28, 1978

INVENTOR(S) : John G. Atwood; CHarles F. DeMey, III & Hamilton W. Marshall Jr., & Lucien C. Ducret It is certified that error appears in the above-identified patent and that said Letters Patent are hereby corrected as shown below:

Column 4, line 67, before "and" insert -- 517 --.

Column 8, line 4, change "seen" to --been--.

Signed and Sealed this

Fifth Day of December 1978

[SEAL]

Attest:

RUTH C. MASON
Attesting Officer

DONALD W. BANNER
Commissioner of Patents and Trademarks